Figure 1:
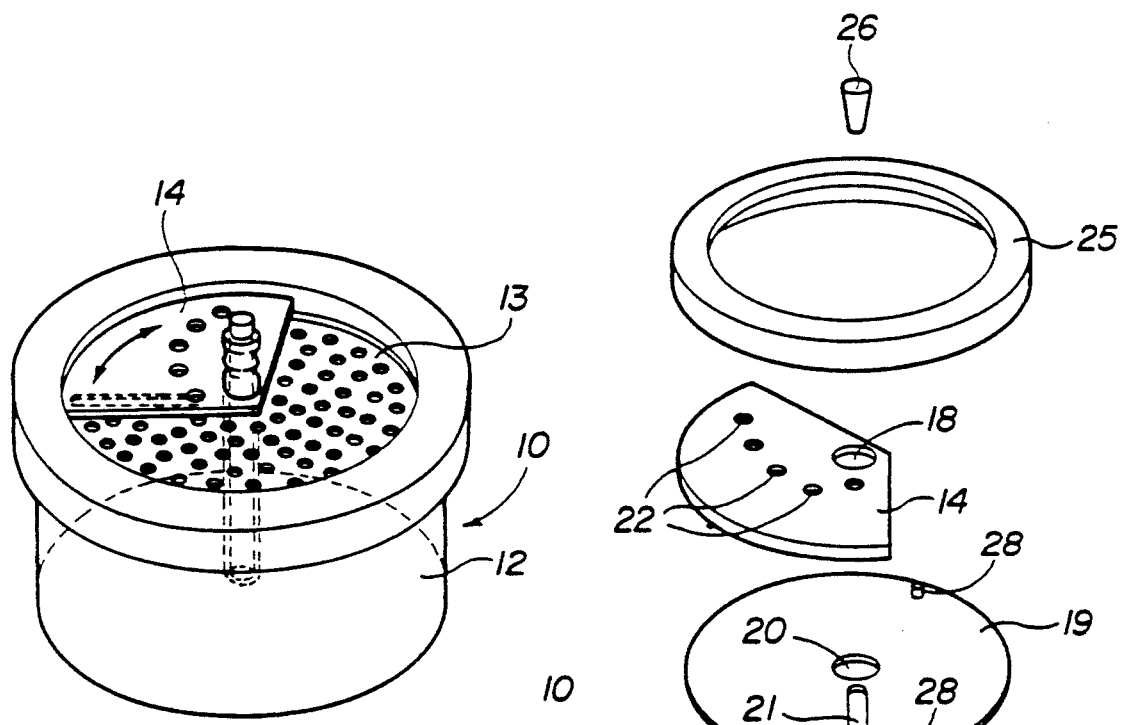

United States Patent

Guignet et al.

[11] Patent Number: 5,307,933
[45] Date of Patent: May 3, 1994

[54] DEVICE FOR PACKAGING AND DISTRIBUTING STERILE OBJECTS

[76] Inventors: Jean-Daniel Guignet, Chemin du Genevrey, CH - 1603 Grandvaux; Sohan Modak, 6, rue Curtat, CH - 1005 Lausanne, both of Switzerland

[21] Appl. No.: 849,423
[22] PCT Filed: Sep. 9, 1991
[86] PCT No.: PCT/CH91/00194
   § 371 Date: Jul. 7, 1992
   § 102(e) Date: Jul. 7, 1992
[87] PCT Pub. No.: WO92/04255
   PCT Pub. Date: Mar. 19, 1992

[30] Foreign Application Priority Data
   Sep. 10, 1990 [FR] France ................. 90 11300

[51] Int. Cl.⁵ .................. B65D 85/20; B01L 9/06
[52] U.S. Cl. .................. 206/443; 206/562; 206/569; 422/64; 422/102
[58] Field of Search ............... 206/443, 446, 562, 563, 206/569, 315.9, 524.8; 422/64, 99, 102, 104

[56] References Cited

U.S. PATENT DOCUMENTS

| | | | |
|---|---|---|---|
| 1,038,355 | 9/1912 | Hamilton | 206/443 |
| 1,060,979 | 5/1913 | Hamilton | 206/443 |
| 1,151,076 | 8/1915 | Wheeler | 206/443 |
| 1,455,492 | 5/1923 | James | 206/443 |
| 3,620,409 | 11/1971 | Rosenbaum | 206/524.8 |
| 4,028,930 | 6/1977 | Moreno | 206/443 |
| 4,093,009 | 6/1978 | Iavarone et al. | 206/524.8 |
| 4,276,258 | 6/1981 | Ginsberg et al. | 422/64 |
| 4,902,626 | 2/1990 | Käymkö et al. | 422/64 |
| 5,008,084 | 4/1991 | Kelley | 422/102 |

FOREIGN PATENT DOCUMENTS 2821346 11/1979 Fed. Rep. of Germany .
2935070 3/1981 Fed. Rep. of Germany .

*Primary Examiner*—Paul T. Sewell
*Assistant Examiner*—M. D. Patterson
*Attorney, Agent, or Firm*—Davis, Bujold & Streck

[57] ABSTRACT

The device comprises a housing (12) containing a support (13) from which the sterile objects (11) hang, said objects being placed in rows of holes, a movable selector (14) arranged to allow at least one object to be reached, and an arrangement for sealing said housing. A sealing plate (19) is mounted between the selector (14) and the support (13) and is provided with a central opening (20) and a radial slot (21) designed to cooperate with the holes (22) in the selector (14). The device can be connected to a vacuum pump via the hollow shaft (16) when the sealing plug (26) is removed.

6 Claims, 3 Drawing Sheets

DEVICE FOR PACKAGING AND DISTRIBUTING STERILE OBJECTS

This invention concerns a device for packaging and distributing sterile objects.

The sterile objects which require specific conditions for packaging and distribution notably include injection needles for syringes and conical and elongated tips used for transferring determined volumes of liquid substances used in biological and/or medical applications.

For biotechnological studies and medical diagnostics, it is frequently required to transfer known volumes of liquid from one test-tube to another under sterile conditions. This makes it obligatory to use sterile objects made for one-time use. These objects are adapted to an apparatus such as an automatic pipette which comprises a movable piston driving a volume of air sufficient to aspirate a volume of liquid equivalent to the volume of air displaced by the moving piston. It is obvious that, to conserve the sterile conditions, the objects must be manipulated with certain precautions. At present, the tips are supplied by specialized companies in flexible bags made of a synthetic material or in boxes containing supports, these tips being arranged so that their larger diameter is directly accessible from above.

This packaging presents as a major drawback the fact that upon opening the box, or the bag, to permit removal of one tip, all tips come in contact with ambient air or, in some cases, with operator's fingers which compromises the sterility of these tips. If the sterile conditions are not maintained then these tips must be washed and autoclaved again prior to each use. Even if these operations are effected after each withdrawal of tips, the remaining tips are deteriorate if they are subjected to several successive cycles of autoclaving.

It is also necessary to envisage a particular packaging using the same criteria as those required in the medical discipline for electronic chips and integrated circuits which are now currently used in the manufacture of computer components.

In consequence, the present invention proposes to overcome the disadvantages of earlier devices by presenting a device which allows conservation of sterile or clean conditions for the packaged objects even if these are withdrawn regularly at shorter or longer interval of time.

This aim is met by the device according to the invention characterized in that it comprises a sterile and autoclavable case, a support provided to hold said objects, a movable selector provided to render free access to at least one object and means to ensure a hermetic closure of the case.

According to a form of realization in which the case is substantially cylindrical, the support comprised a plate with holes in which said objects are deposited, the movable selector is rotatable around a central axis passing through the centre of the support and comprises at least one hole placed in such a way that it can be brought to coincide with all of the objects deposited in the holes on the support plate, and the means to ensure a hermetic closure of the case comprises at least one closing plate movable around said axis and in which at least one opening is provided which can be brought to coincide with the hole in the selector.

Preferably, the support plate comprises holes arranged in circles concentric to the central axis, the selector comprises as many holes as the support plate comprises concentric circles, and the closing plate comprises a radial slit whose length corresponds to at least the distance between the concentric circle of the smallest diameter and that of the largest diameter.

According to this embodiment, the central axis is hollow and comprises at least one opening at the external extremity designed to be connected with a vacuum pump, and at least one opening located inside the case. This opening inside the case may be located below the closing plate.

According to another particularly advantageous embodiment, the device comprises a case provided with cavities to house the objects, a movable sector designed to give access to at least one object and a closing plate to ensure a hermetic closure of this case.

According to another form of realization in which the case is a rectangular parallelpiped, the support is comprised of a rectangular plate provided with rows of holes in which said sterile objects are held, the movable selector is comprised of a series of parallel sliding strips whose number is the same as the number of rows of holes on the support plate, and the case comprises a neutral zone whose width corresponds to one row of objects.

In this form of realization, the width of each sliding strip is substantially equal to the width of each row of objects and, in the closed position, all the strips together cover all the rows of objects.

Figure 2:
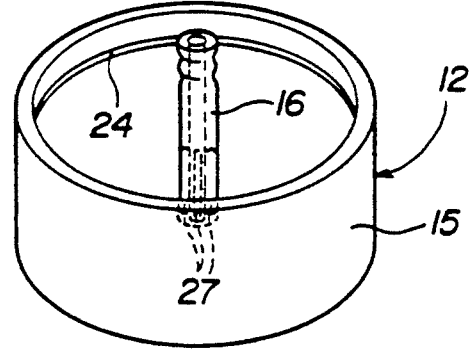

The present invention will be better understood with reference to the description of examples of realizations and to the annexed drawings in which:

FIG. 1 represents a perspective view of an advantageous embodiment of the device according to the invention, FIG. 2 represents an exploded view of the device illustrated in FIG. 1.

Figures 2A, 2B:
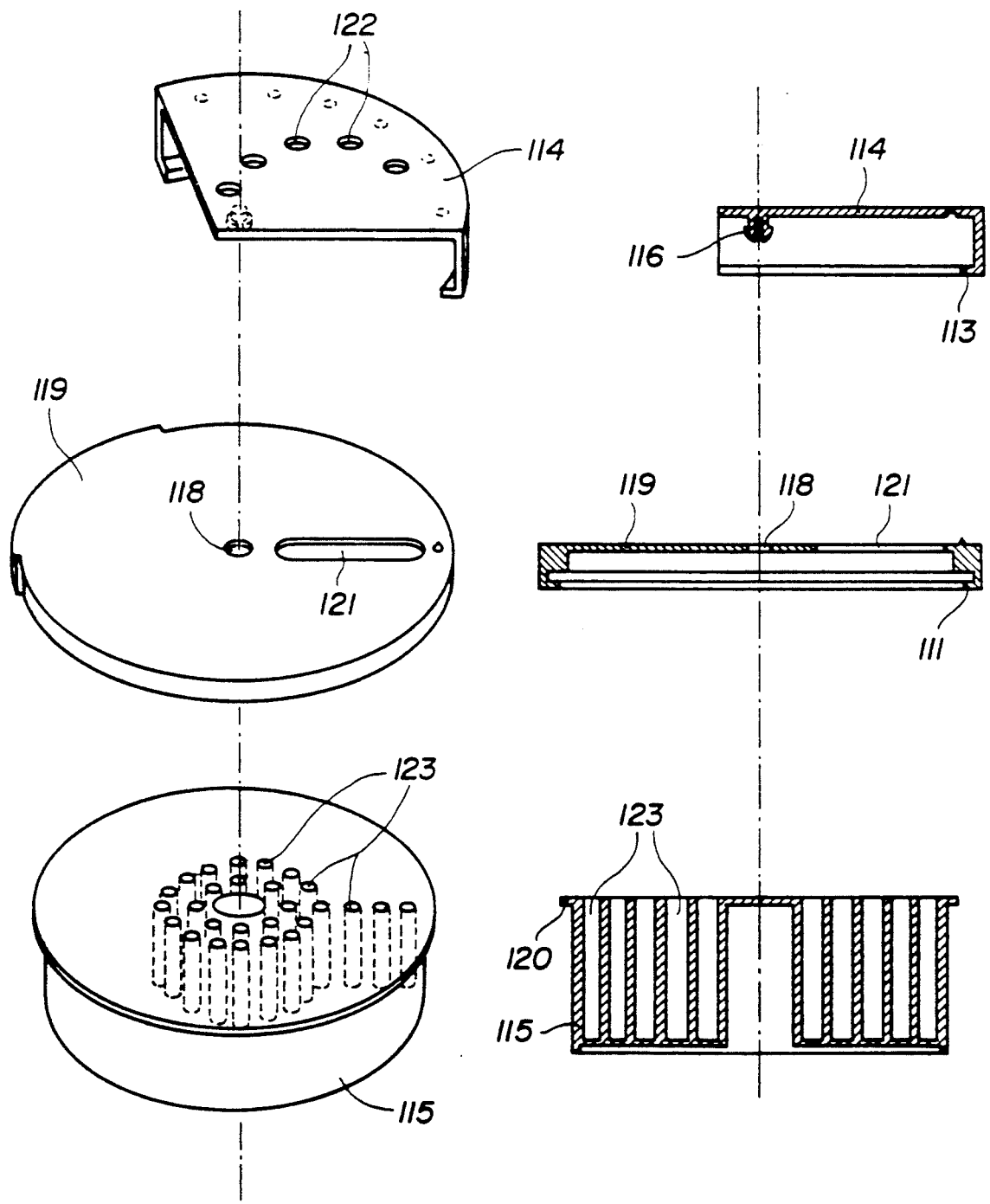
Figure 3:
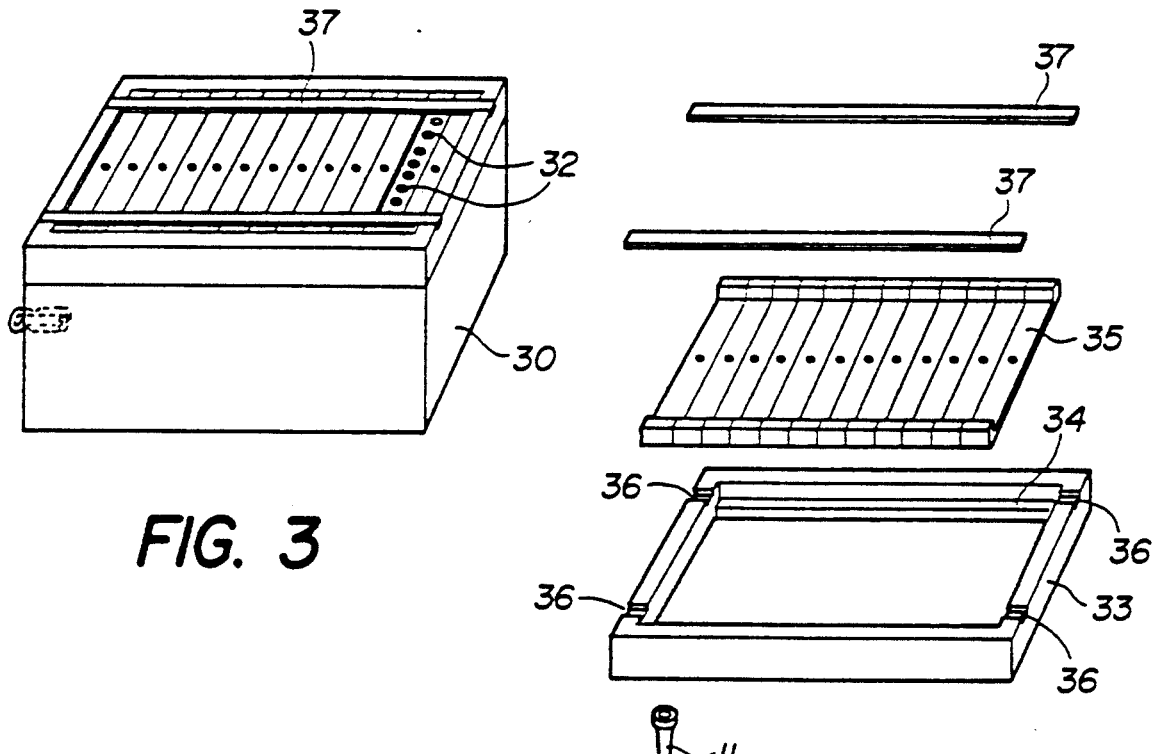
Figure 4:
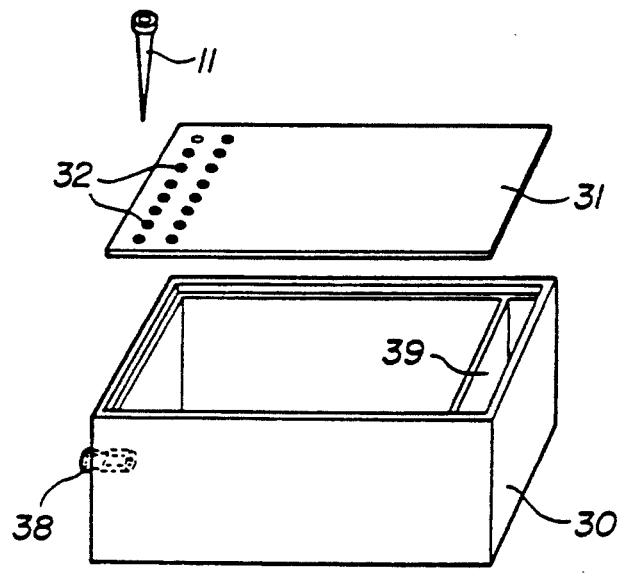
Figure 5:
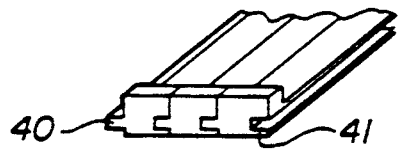

FIG. 2A represents an exploded view of a simplified form of the device illustrated in FIG. 1, FIG. 2B represents a section view of the elements of the device of FIG. 2A, FIG. 3 represents a perspective view of another embodiment of the device according to the invention, FIG. 4 represents an exploded view illustrating the main components of the device of FIG. 3, and FIG. 5 represents a partial perspective view of a detail of the device of FIGS. 3 and 4.

With reference to FIGS. 1 and 2, the device 10 for packaging and distributing the elongated and conical sterile objects 11, essentially comprises a case 12, containing a support 13 designed to hold the said objects in rows of holes, a movable selector 14 designed to provide aces to at least one object, and with means of ensuring a hermetic closure of the said case. When the stored objects are conical pipette tips, these tips are suspended in the holes of the support 13 by their largest extremity.

The case has a substantially cylindrical shape and at the centre of its base 15 is fixed an (axle) 16 which passes through a central opening 17 of the support 13 and also through a central opening 18 of the selector 14. Between the selector 14 and the support 13 is mounted a closing plate 19 having a central opening 20 in which the axis 16 is engaged, and a radial slit 21 which coincide with the holes 22 made in the selector 14. It should be noted that the different holes 22 are radially staggered with reference to the opening 18 in such a way that each one corresponds to one of the rows of holes 23 of the support 13. This support is resting against a shoulder 24 provided in the lateral wall of the case 12. It is covered by a closing plate 19 and all of these different elements are maintained in place by a ring-shaped element. 25.

The axis 16 is hollow and its upper extremity is closed by a plug 26. The axis can be connected when the closing plug 26 is removed, with a vacuum pump which allows the creation of a vacuum inside the case. To this aim, this axis comprises in its base a certain number of axial slits or holes 27 which allow the communication between the interior of the case with the conduit inside the axis 16.

To remove a sterile object contained in the case 12, the selector 14 is rotated in such a way that the openings 22 coincide with the slit 21 of the closing plate 19, this slit coinciding with the holes in the support 13 and consequently with the lager extremities of the objects 11, when these objects are tips held in these holes. Two stopping points 28 on the plate 19 limit the lateral displacement of the movable selector 14. In the case of packaging of tips for the transfer of volumes of liquids, an apparatus such as an automatic pipette is fitted on the said tip. The pint of this tip is then dipped into the liquid to be taken and the piston of the automatic pipette is displaced to aspirate a predetermined volume of this liquid. In order to avoid contamination of the liquid in which the tip is dipped, it is essential that the tip should be sterile. Furthermore, this dispenser tip should also be sterile to avoid contamination of the removal volume of liquid destined to be transferred for a biological or medical application. In the above-described device, this requirement can be satisfied due to the fact that it is possible to select only one tip without the risk of contaminating the other tips. The suppression of the movable selector 14 allows access a full row of dispenser tips.

The device illustrated by the FIGS. 2A and 2B is a simplified version of the device described with reference to FIGS. 1 and 2 in that it comprises only three elements and cannot be connected with a vacuum pump. In this embodiment, the device consists of a case 115 comprising a series of cylindrical cavities 123, the diameter and depth of which can vary according to the object to be packaged, a closing plate 119 provided with a radial slit 121, and a movable selector 114 with holes 122 which cooperate with the radial slit 121 of the closing plate 119. This closing plate 119 comprises a central opening 118 which acts with a pin 116 of the movable selector 114 thus allowing interaction between these two elements, as well as a edge with a rim 111 which allows the plate to be fixed on the case 115 by ratching of this on the projecting edge 120 of the case. The movable selector 114 is then ratched with the totality of the system composed of the case and the closing plate by means of its edge with a rim 113. The removal of the sterile objects is done in the same way as described for the above device. The advantage of this device resides in the fact that its three elements can be made by moulding, and therefore have relatively low manufacturing costs.

With reference to FIGS. 3 and 4, the device comprises as before, a case 30 which, in the present case, has the form of a parallelpiped rectangle. Inside this case is mounted a support 31 of the shape of a rectangular plate on which are arranged rows of holes 32 destined to hold sterile objects. A frame 33 for holding in place the support 31 is fitted on the upper edge of the case 30. This frame 33 comprises two laterally grooves 34 which support a series of sliding strips 35 whose number is the same as the rows of holes 32 arranged in the support 31. The width of a sliding strip 35 is substantially the same as the width of each row of holes 32. Additionally, the frame 33 comprises notches 36 in which are positioned two longitudinal guides 37, which ensure the maintenance and guidance of sliding strips 35. Moreover, the case 30 is equipped with a tubular exit 38 which allows it to be connected with a vacuum pump.

This device has been conceived to allow simultaneous removal of a number of sterile objects and especially those in a complete row of holes. In the closed position, the sliding strips 35 completely cover a row of holes 32 i.e. the upper orifices of the sterile objects 11. When a user wishes to withdraw one row of these objects, he displaces the first sliding strip 35 over the neutral zone 39 arranged in the case and not covered by the support plate 31. In this manner, he frees the first row of holes 32 and consequently the first row of sterile objects 11. These objects can be removed with a known device. When the user wishes to gain access to the following row, he displaces the second sliding strip which will then cover the first row from where the objects had previously been withdrawn. He continues in this manner, i.e. by successively displacing the third, the fourth and the n th sliding strip 35 to successively gain access to the rows of sterile objects.

According to a variant of realization not shown here, a second series of sliding strips could be arranged perpendicular to the first series 35 which would allow access to a single object instead of an entire row.

The sliding strips shown in the FIG. 5 can be interlocked and for this purpose carry a rib 40 along one of its edges and a groove 41 along the opposite edge.

Also in realizations which are not shown here, the movable selector, the closing plate and the support plate of the device described with reference to FIGS. 1 and 2 can be made with a rim allowing their fixation on the case by a ratchet-motion such as that described with reference to the device illustrated by FIGS. 2A and 2B. One can also realize devices in which the case has a section which is polygonal, for example square, triangular, hexagonal, etc.

We claim:

1. A device, for packaging and distributing sterile objects, comprising a substantially cylindrical sterile case, a circular support member being located in said sterile case and being provided with holes in which the sterile objects are to be deposited, a movable selector being rotatable around a longitudinal central axis passing through a center of said support member and comprising at least one hole which can be brought to coincide with a desired sterile object when deposited in one of said holes of said support member, and means for forming a hermetic closure of said sterile case, wherein said means for forming hermetic closure of said sterile case comprises at least one closing plate, rotatable around said central axis, with at least one opening provided in said at least one closing plate, said at least one opening is movable to coincide with said at least one hole of said selector to facilitate access to a desired sterile object.

2. A device according to claim 1, wherein said holes of said support member are arranged in circular rows concentric with said central axis, said selector comprising a respective hole for each of said circular rows, and said opening of said closing plate comprising a radial slit extending across all of said circular rows.

3. A device according to claim 1, wherein said circular support member is a support plate mounted within said sterile case.

4. A device according to claim 3, wherein said central axis is defined by a hollow axis member and said hollow axle member has at least one opening arranged outside said sterile case for connection to a vacuum source, and at least one opening located inside said sterile case.

5. A device according to claim 4, wherein said at least one opening located inside said sterile case is located between said support plate and a base of said sterile case.

6. A device, for packaging and distributing sterile objects, comprising a substantially cylindrical sterile case, a circular support member being located in said sterile case and being provided with holes in which the sterile objects are to be deposited, a movable selector being rotatable around a longitudinal central axis passing through a center of said support member and comprising at least one hole which can be brought to coincide with a desired sterile object when deposited in one of said holes of said support member, and means for forming a hermetic closure of said sterile case, wherein said means for forming hermetic closure of said sterile case comprises at least one closing plate, rotatable around said central axis, with at least one opening provided in said at least one closing plate, said at least one opening is movable to coincide with said at least one hole of said selector to facilitate access to a desired sterile object, said sterile case is autoclavable, and said circular support member is integral with said sterile case.

* * * * *